(12) United States Patent
Binder

(10) Patent No.: US 6,862,535 B2
(45) Date of Patent: Mar. 1, 2005

(54) FOURIER TRANSFORM INFRARED (FTIR) SPECTROMETRIC TOXIC GAS MONITORING SYSTEM, AND METHOD OF DETECTING TOXIC GAS SPECIES IN A FLUID ENVIRONMENT CONTAINING OR SUSCEPTIBLE TO THE PRESENCE OF SUCH TOXIC GAS SPECIES

(76) Inventor: Robin L. Binder, 1584 Howard Ave., San Carlos, CA (US) 94070

( * ) Notice: Subject to any disclaimer, the term of this patent is extended or adjusted under 35 U.S.C. 154(b) by 143 days.

(21) Appl. No.: 10/218,551

(22) Filed: Aug. 14, 2002

(65) Prior Publication Data

US 2004/0034480 A1 Feb. 19, 2004

(51) Int. Cl.$^7$ ............................................. G01N 31/00
(52) U.S. Cl. ...................................................... 702/24
(58) Field of Search .............................. 702/22–24, 40, 702/45, 49, 50, 69, 75–77, 100; 73/23.2, 30.04; 356/440, 450, 451

(56) References Cited

U.S. PATENT DOCUMENTS 5,777,735 A * 7/1998 Reagen ........................ 356/451
6,134,004 A * 10/2000 Reagen et al. ............... 356/451
6,748,334 B1 * 6/2004 Perez et al. ..................... 702/24

* cited by examiner

*Primary Examiner*—Michael Nghiem
(74) *Attorney, Agent, or Firm*—Yongzhi Yang; Steven J. Hultquist; Marianne Fuierer

(57) ABSTRACT

An FT-IR toxic gas monitoring system and method for detection of one or more toxic gas species in a fluid environment containing or susceptible to presence of toxic gases. Such gas monitoring system includes: (1) a spectroscopic monitoring assembly for transmitting modulated infrared radiation through a spectroscopic cell that contains a gas sample from such fluid environment and generating a corresponding digitized spectrum characteristics of such gas sample for analysis; (2) a gas sampling and delivery subsystem for sampling the fluid environment and delivering the gas sample to the spectroscopic cell; and (3) a computational assembly (i) including a stored signal-to-noise ratio reference, and a stored background spectrum for the fluid environment when the toxic gas species is not present, and (ii) arranged to analyze the digitized spectrum and responsively produce an output indicative of quantitative presence of the toxic gas species in the fluid environment.

54 Claims, 5 Drawing Sheets

FOURIER TRANSFORM INFRARED (FTIR) SPECTROMETRIC TOXIC GAS MONITORING SYSTEM, AND METHOD OF DETECTING TOXIC GAS SPECIES IN A FLUID ENVIRONMENT CONTAINING OR SUSCEPTIBLE TO THE PRESENCE OF SUCH TOXIC GAS SPECIES

BACKGROUND OF THE INVENTION

1. Field of the Invention

The present invention relates to a Fourier Transform Infrared (FTIR) spectrometric toxic gas monitor system, and associated method of detecting toxic gas species in an environment containing or susceptible to the presence of same, such as a gaseous effluent stream produced from a semiconductor manufacturing operation, or a clean room gaseous environment or an industrial processing facility in which air quality is monitored for the presence of toxic gas components therein.

2. Description of the Related Art

In any spectroscopic technique, such as FTIR, for monitoring a fluid environment for the presence of toxic components, the quality of the background spectrum is important.

Such background spectral quality is particularly critical for reliable operation of a toxic gas monitor, which is provided to operate continuously in an unattended manner.

Continuous measurement of the quality of the background spectrum during gas monitoring, in addition to facilitating continuous, unattended operational reliability, also enables the monitoring system to be operated so that a user or operator can be alerted of the need for system maintenance before problems such as false positive alarms occur.

In addition to deficiencies of background spectrum monitoring that are characteristic of conventional FTIR toxic gas monitoring systems, as lacking effective and reliable background monitoring capability, typical problems involving FTIR toxic gas monitoring systems include contamination of optical components such as mirrors or windows, noisy spectra and weak IR source intensity.

SUMMARY OF THE INVENTION

The present invention relates generally to FTIR gas monitoring systems and methods of an improved character, relative to the above-described deficiencies and operational problems of the prior art.

In one aspect, the present invention relates to an FT-IR toxic gas monitoring system for detection of one or more toxic gas species in a fluid environment containing or susceptible to presence of same. The system comprises:

an FT-IR monitoring assembly including a gas flow path, an FT-IR cell in gas flow communication with the gas flow path, an infrared radiation source, an interferometer arranged in receiving relationship to the infrared radiation source to modulate infrared radiation and transmit correspondingly modulated infrared radiation through the FT-IR cell for absorption of the correspondingly modulated infrared radiation characteristic of said toxic gas species when present in gas flowed through the FT-IR cell, a detection unit arranged in relation to the FT-IR cell to receive non-absorbed radiation therefrom and produce a corresponding digitized spectrum for analysis;

means for sampling the fluid environment and delivering samples therefrom to the gas flow path for flow to the FT-IR cell; and a computational assembly (i) including a stored signal-to-noise ratio reference, and a stored background spectrum for the fluid environment when the toxic gas species is not present therein, and (ii) arranged to analyze the digitized spectrum and responsively produce an output indicative of quantitative presence of the toxic gas species in the fluid environment, in an analysis procedure comprising continuous measurement of the quality of a background spectrum of a monitored spectral region for the fluid environment, and determination of:

(a) signal-to-noise ratio from signal and noise characteristics of the digitized spectrum, and deviation from the stored signal-to-noise reference;

(b) a background spectrum for the monitored fluid environment excluding the toxic gas species, if any, therein, and deviation from the stored background spectrum; and (c) a zero path difference for the detection unit.

In another aspect, the invention relates to a method of toxic gas monitoring for detection of one or more toxic gas species in a fluid environment containing or susceptible to presence of same. The method comprises:

sampling the fluid environment to provide samples for analysis;

spectrometrically analyzing the samples by FT-IR analysis and generating a corresponding digitized spectrum;

providing a programmable computer including data storage containing a stored signal-to-noise ratio reference, and a stored background spectrum for the fluid environment when the toxic gas species is not present therein;

programmatically analyzing the digitized spectrum via the programmable computer and responsively producing an output indicative of quantitative presence of the toxic gas species in the fluid environment, in an analysis procedure comprising continuously measuring the quality of a background spectrum of a monitored spectral region for the fluid environment, and determining:

(a) signal-to-noise ratio from signal and noise characteristics of the digitized spectrum, and deviation from the stored signal-to-noise reference;

(b) a background spectrum for the monitored fluid environment excluding the toxic gas species, if any, therein, and deviation from the stored background spectrum; and (c) a zero path difference for the detection unit.

Other aspects, features and advantages of the invention will be more fully apparent from the ensuing disclosure and appended claims.

DETAILED DESCRIPTION OF THE INVENTION, AND PREFERRED EMBODIMENTS THEREOF

The present invention relates to spectroscope monitoring systems such as an FTIR toxic gas monitoring system and method for high-reliability detection of toxic gas species in a monitored fluid environment.

Figure 6:
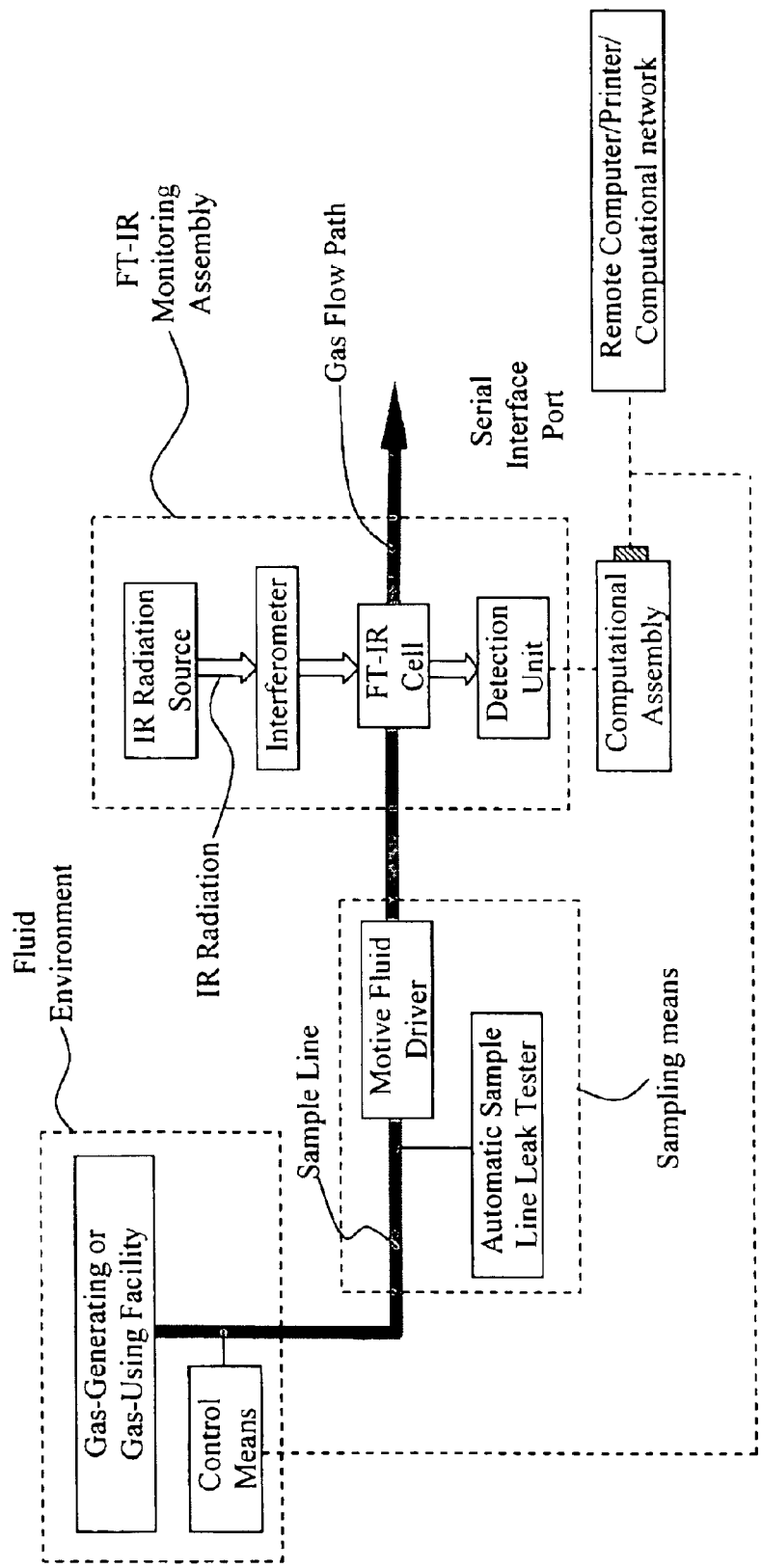
FIG. 6 is a schematic view of an FT-IR toxic gas monitoring system according to one embodiment of the invention.

The present invention provides an FT-IR toxic gas monitoring system for detection of one or more toxic gas species in a fluid environment containing or susceptible to presence of same. A specific embodiment of such FT-IR toxic gas monitoring system is schematically illustrated in FIG. 6, which includes:

an FT-IR monitoring assembly including a gas flow path, an FT-IR cell in gas flow communication with the gas flow path, an infrared radiation source, an interferometer arranged in receiving relationship to the infrared radiation source to modulate infrared radiation and transmit correspondingly modulated infrared radiation through the FT-IR cell for absorption of the correspondingly modulated infrared radiation characteristic of said toxic gas species when present in gas flowed through said FT-IR cell, a detection unit arranged in relation to said FT-IR cell to receive non-absorbed radiation therefrom and produce a corresponding digitized spectrum for analysis;

means for sampling the fluid environment and delivering samples therefrom to said gas flow path for flow to the FT-IR cell; and a computational assembly (i) including a stored signal-to-noise ratio reference, and a stored background spectrum for the fluid environment when the toxic gas species is not present therein, and (ii) arranged to analyze the digitized spectrum and responsively produce an output indicative of quantitative presence of the toxic gas species in the fluid environment, in an analysis procedure comprising continuous measurement of the quality of a background spectrum of a monitored spectral region for said fluid environment, and determination of:

(a) signal-to-noise ratio from signal and noise characteristics of said digitized spectrum, and deviation from the stored signal-to-noise reference;

(b) a background spectrum for the monitored fluid environment excluding the toxic gas species, if any, therein, and deviation from the stored background spectrum; and (c) a total detector signal, such as zero path difference for the detection unit.

In one embodiment, the computational assembly (i) further stores setpoint information for signal-to-noise ratio, and (ii) is constructed and arranged to output a service alert if the deviation of signal-to-noise ratio of said digitized spectrum from the stored signal-to-noise reference deviates from a setpoint determinable from said setpoint information by more than a predetermined extent.

In another embodiment, the computational assembly (i) further stores setpoint information for deviation of background spectrum for the monitored fluid environment excluding the toxic gas species, if any, therein, from the stored background spectrum, and (ii) is constructed and arranged to output a service alert if the deviation of background spectrum for the monitored fluid environment excluding the toxic gas species, if any, therein, from the stored background spectrum, deviates from a setpoint determinable from said setpoint information by more than a predetermined extent.

In still another embodiment, the computational assembly (i) further stores setpoint information for the zero path difference, and (ii) is constructed and arranged to output a service alert if the zero path difference deviates from a setpoint determinable from said setpoint information by more than a predetermined extent.

Thus, the computational assembly may be constructed and arranged to monitor at least one of (a), (b) and (c) as a function of time, over an extended period of operation, and to provide an output warning a user of gradual degradation of the system and method so that maintenance and/or other compensatory action can be taken. For example, the computational assembly may be constructed and arranged to monitor each of (a), (b) and (c) as a function of time.

In the above-described FT-IR toxic gas monitoring system, the computational assembly in one illustrative embodiment includes a stored signal-to-noise ratio reference for at least one of toxic gas species selected from the group consisting of ammonia ($NH_3$), arsine ($AsH_3$), boron trifluoride ($BF_3$), boron trichloride ($BCl_3$), carbon monoxide (CO), diborane ($B_2H_6$), dichlorosilane ($SiCl_2H_2$), germane ($GeH_4$), hydrogen bromide (HBr), hydrogen chloride (HCl), hydrogen fluoride (HF), hydrogen selenide ($H_2Se$), methane ($CH_4$), nitric acid ($HNO_3$), nitric oxide (NO), nitrous oxide ($N_2O$), nitrogen dioxide ($NO_2$), nitrogen trifluoride ($NF_3$), phosphine ($PH_3$), phosphorous oxychloride ($POCl_3$), silane ($SiH_4$), silicon tetrafluoride ($SiF_4$), silicon tetrachloride ($SiCl_4$), sulfur hexafluoride ($SF_6$), trichlorosilane ($SiCl_3H$), tungsten hexafluoride ($WF_6$), chloroform ($CHCl_3$), diethyl telluride ($Te(C_2H_5)_2$), hexafluoroethane ($C_2F_6$), hexamethyldisilizane (HMDS), methylsilane ($SiH_3(CH_3)$), dimethylsilane ($SiH_2(CH3)_2$), trimethylsilane ($SiH(CH_3)_3$), tetramethylsilane ($Si(CH_3)_4$), methyl chloride ($CH_3Cl$), methyl fluoride ($CH_3F$), octoafluorocyclopentene ($C_5F_8$), tert-butyl arsine ($As(t-Bu)H_3$), tert-butyl phosphine ($P(t-Bu)H_3$), tetraethylorthosilicate (TEOS), tetrafluoromethane ($CF_4$), trimethylarsenic ($As(CH_3)_3$), trimethyl borate ($B(CH_3)_3$) and trimethyl phosphite ($P(CH_3)_3$), acetic acid ($CH_3COOH$), ethanolamine, methylene chloride, butyl cellosolve, ethylene glycol monobutyl ether acetate, propylene glycol monomethyl ether acetate, acetonitrile, ethylene glycol monoethyl ether, methyl ethyl ketone, acetone, ethyl acetate, methyl isobutyl ketone, n-butyl acetate, ethanol, n-methyl-2-pyrrolidone, carbon tetrachloride, ethyl benzene, perchloroethylene, carbon tetrafluoride, ethylene diamine, phenol, cellosolve acetate, ethylene glycol, trichlorobenzene, chlorobenzene, ethyl lactate, 1,1,1-trichloroethane, cyclohexane, formaldehyde, trichloroethylene, cyclohexanone, isopropanol, trifluoromethane, dichlorobenzene, methanol, triethylene glycol, 1,2-dichloroethylene, methyl cellosolve, xylenes (ortho, meta, para), dimethyl acetamide and methyl cellosolve acetate.

In another embodiment of the FT-IR toxic gas monitoring system of the invention, the computational assembly includes a stored signal-to-noise ratio reference for at least one of toxic gas species selected from the group consisting of organic compounds, metalorganic compounds, halocarbon compounds, inorganic halides, inorganic oxides, and inorganic hydrides.

The FT-IR toxic gas monitoring system may be constructed and arranged with a computational assembly that includes a stored signal-to-noise ratio reference for at least one toxic gas species having a time-weighted average threshold limit value (TWA-TLV) of one part-per-million (ppm) by volume or higher. The FT-IR toxic gas monitoring system may be adapted for sampling multiple gas species from the fluid environment, and the computational assembly can include a computational central processing unit (CPU) that is reprogrammable to add or delete predetermined permanent calibration data for toxic gas species, for adaptation of the system to change in a monitored fluid environment.

The FT-IR toxic gas monitoring system of the invention does not comprise a pyrolyzer to convert gases to HF for detection.

The computational assembly of the FT-IR toxic gas monitoring system may include dry contact relay outputs including multiple relays, programmable by sample points and gas type(s). The computational assembly in one embodiment includes at least one serial interface port, e.g., an RS-232 port and/or an RS-485 port, for connection with remote computer and/or printer equipment, as shown in FIG. 6. Such serial interface port(s) may be coupled with a computational network.

The FT-IR toxic gas monitoring system can be constructed with a computational assembly that is adapted to conduct continuous scan FT-IR analysis, e.g., of toxic gas species such as organics, metalorganics, perfluorocarbons (PFCs), chlorofluorocarbons (CFCs), hydrofluorocarbons (HFCs), and inorganic gases.

In the FT-IR toxic gas monitoring system of the invention, the output indicative of quantitative presence of the toxic gas species in the fluid environment may for example have a lower detection limit in a range of from about 0.1 to about 2.0 ppm (by volume), and/or a range of analysis of the toxic gas species that is equal to or in a range of from about 0 to about 250 ppm (by volume).

In a preferred embodiment, the FT-IR toxic gas monitoring system includes a unitary cabinet at least partially enclosing each of the FT-IR monitoring assembly, means for sampling the fluid environment and delivering samples therefrom to the gas flow path for flow to the FT-IR cell, and the computational assembly.

The means for sampling the fluid environment and delivering samples therefrom to the gas flow path for flow to the FT-IR cell, may include means of any suitable type, including appropriate flow circuitry (piping, conduits, manifolds, couplings, mass flow controllers, instrumentation, etc.), motive fluid drivers (e.g., venturi pumps, mechanical pumps, venturi pumps and mechanical pumps in combination, wherein the venturi pump is operatively coupled with switches, solenoids, relays, or other means for automatic switchover to the mechanical pump, blowers, fans, compressors, etc.) and the sample flow lines of the system optionally may be equipped with automatic sample line leak test units, for automatically testing the leak-tightness of the gas flow path, at predetermined time intervals, as shown in FIG. 6.

The FT-IR toxic gas monitoring system of the invention may be operated so that the output indicative of quantitative presence of the toxic gas species in the fluid environment, is transmitted to control means (mass flow controllers, restricted flow modulating devices, valves, manifolding, recirculation loops, flow diverter passages, alarm and shutdown means, alarm relay and outputting means, holding tank fill volume controllers, etc.) of a gas-generating or gas-using facility (see FIG. 6), to responsively control same.

In one embodiment, the FT-IR toxic gas monitoring system of the invention is coupled in gas monitoring relationship to a semiconductor manufacturing process unit having a fluid environment associated therewith. The fluid environment may for example be constituted by a gas stream that is produced or used in a semiconductor manufacturing process unit. Various semiconductor manufacturing plant environments may advantageously be monitored by the monitoring system of the invention, e.g., gas environments of gas cabinets, process tools, valve manifold boxes, vacuum pumps, and exhaust ducts.

The monitoring system of the invention thus is operable to effect a method of toxic gas monitoring for detection of one or more toxic gas species in a fluid environment containing or susceptible to presence of same, by steps including:

sampling the fluid environment to provide samples for analysis;

spectrometrically analyzing such samples by FT-IR analysis and generating a corresponding digitized spectrum;

providing a programmable computer, e.g., a programmable general purpose computer, including data storage containing a stored signal-to-noise ratio reference, and a stored background spectrum for the fluid environment when the toxic gas species is not present therein;

programmatically analyzing the digitized spectrum via said programmable computer and responsively producing an output indicative of quantitative presence of the toxic gas species in the fluid environment, in an analysis procedure comprising continuously measuring the quality of a background spectrum of a monitored spectral region for the fluid environment, and determining:

(a) signal-to-noise ratio from signal and noise characteristics of the digitized spectrum, and deviation from the stored signal-to-noise reference;

(b) a background spectrum for the monitored fluid environment excluding the toxic gas species, if any, therein, and deviation from the stored background spectrum; and (c) a zero path difference for the detection unit.

The system and method of the invention are broadly applicable to monitoring of gases for hazardous component(s) in industrial environments. In application to semiconductor manufacturing operations, the system and method of the invention may be variously employed for detection of semiconductor process gas components in breathing air in the semiconductor manufacturing facility, and detection of such gas components in gas environments of gas cabinets, process tools, valve manifold boxes, vacuum pumps, exhaust ducts and the like. The system and method of the invention are also usefully employed to monitor stack gases, plant emissions, chemical storage rooms, etc., in a wide variety of industrial operations.

The gas monitoring system and method of the invention is usefully employed to monitor a broad range of chemicals, and helps to identify unknown odors, specifically identifies each gas, eliminates phantom false alarms, adapts to changes in tool chemistries, and is capable of monitoring a large number of gas sampling points (e.g., 10, 20, 30, 40 or more sample points), all without requirement of on-site gas calibration.

The FTIR gas monitoring system and method of the invention continuously measure the quality of a background spectrum of the monitored spectral region, by measuring:

1) Signal-to-noise Ratio.

Typically, the signal-to-noise (S/N) value is taken from a spectrum that has already been referenced to a background, presented as % Transmittance, and calculated from the peak-to-peak noise level in the spectrum by the following equation:

$$S/N = 1.41/(pk\text{—}pk \text{ noise, } \% T)$$

wherein:
pk—pk noise is peak-to-peak noise in units of % T; and
T is the __% Transmittance.

The signal-to-noise ratio itself is dimensionless. It is a ratio of two numbers with the same units where signal and noise are assumed to be in units of 1% T. The factor 1.41 noted above is the square root of two and is a correction for taking the ratio of two separtate spectra, background and sample, in order to get a spectrum expressed in % T.

This conventional type of S/N calculation is a measure of only noise, and actual measured signal level is not involved in the calculation.

The system and method of the present invention measure the average peak-to peak noise in the background spectrum over a short wavelength range. The signal is the actual intensity of the background at this same wavelength level, so that the intensity is a measure of the condition of the optics and the IR source. The system and method of the present invention therefore use a real signal and a real noise level to calculate S/N. If the S/N falls below a setpoint value, a service alert is generated. The S/N value determined in this manner is also graphed as a function of time, over an extended period of operation, to provide a graphical output warning the user of gradual degradation of the system and method so that maintenance and/or other compensatory action can be taken.

2) Background Drift.

In the FTIR toxic gas monitoring system and method of the invention, a current background spectrum typically is compared to a "factory background"—a background spectrum that is determined for an end use application and stored in the computer associated with the monitoring system. Differences between the two spectra—the currently monitored background spectrum and the factory background—can indicate that the optics of the monitoring system are contaminated or that the IR source may require replacement or that the normally clean background gas has changed in composition, physical properties, etc. Such difference is the so-called "drift" of the system. If the drift falls below a setpoint, a service alert is generated. The drift value also is graphed as a function of time, over an extended period of operation, to provide a graphical output warning the user of gradual degradation of the system and method so that maintenance and/or other compensatory action can be taken.

3) Zero Path Difference (ZPD).

The zero path difference signal comes from the FTIR spectrometer and is a measure of the amount of light reaching the detector. This is similar to the background drift measurement but coarser, and thus provides less information than drift determination, but is critical to the use of the system and method of the invention, since it provides essential quantitative monitoring of the light ultimately impinging on the detector. If the ZPD falls below a setpoint, a service alert is generated. In one embodiment, low and high ZPD setpoints are employed to trigger a malfunction relay and to output a corresponding message to output means such as a display screen. The ZPD value also is graphed as a function of time, over an extended period of operation, to provide a graphical output warning the user of gradual degradation of the system and method so that maintenance and/or other compensatory action can be taken.

The output of the toxic gas monitoring system and method of the invention may be employed in an associated gas-generating or gas-using facility to responsively control same, e.g., by operatively linking the gas monitoring system with appropriate control means, such as alarm and shutdown means, alarm relay and outputting means, flow diversion means, mass flow controllers, holding tank fill volume controllers, etc.

The present invention thus provides a toxic gas monitoring system with self-diagnostic features of ZPD testing, S/N testing and background drift testing, which measures and determines the trends of the quality of the background spectra in the monitoring operation. The background spectra may be measured in the practice of the invention at any suitable intervals.

In one embodiment, the background spectra are determined every two hours.

The system and method of the invention in another embodiment are constructed and arranged to provide a graphical output of the ZPD testing for each sample point, and not just for the background. As a consequence, the system and method enable the ready identification of dirty sample points that may require additional filtration beyond normal filtration requirements, in instances where sampling nodes are susceptible to contamination.

The FTIR gas monitoring system and method of the invention enable monitoring of nearly all gases having a time-weighted average threshold limit value (TWA-TLV) of one part-per-million (ppm) by volume and higher. The system and method are applicable to detect multiple gas species (e.g., 10–12 or more) at a single sample point, identifying and quantifying each one.

The FTIR gas monitoring system of the invention preferably is of a character comprising a computational central processing unit (CPU) that is reprogrammable to add or delete gases by simple software changes that involve predetermined permanent calibration data being added or deleted from the active monitoring state of the system, as necessary or desirable in a given end use application of the system and method of the invention.

The FTIR system and method of the invention do not require a pyrolyzer to convert gases to HF for detection, and even if a fluorocarbon converts to HF in the gas environment being monitored, a false alarm condition is avoided.

The FTIR system of the invention includes an interferometer that modulates a beam of infrared light and transmits it through a gas cell containing the gas (air) sample. The gas-borne chemicals in the sample absorb infrared light and the remaining light is reflected to a detector. At the detector, the infrared light is digitized, then computed into an error-free spectrum containing all of the analytical information. The FTIR system's CPU then examines the infrared spectrum, to identify and to quantify each chemical present in the air sample.

The FTIR system of the invention in one embodiment is constructed and arranged with dry contact relay outputs including up to 80 relays, programmable by sample points and gas type(s). Such system includes serial interface ports, which may be for example RS-232 or RS-485 ports, for communication coupling with a remote printer and/or computer. Interface/outputs may be of varying types, including for example Ethernet, LonWorks®, LAN, Analog 4–20 mA, or any other suitable interface/output configurations.

In the aforementioned illustrative embodiment, analysis is carried out by continuous scan FT-IR analysis, and the gas cell path is 10 meters, such characteristic serving to maximize sensitivity of the FT-IR analysis in the specific equipment conformation employed. The gases monitored may include organics, metalorganics, perfluorocarbons (PFCs), chlorofluorocarbons (CFCs), hydrofluorocarbons (HFCs), and various inorganic gases, with all being accommodated by the same apparatus unit.

The lower detection limit of such illustrative embodiment apparatus is 0.1 to 2.0 ppm, with 1.0 ppm (by volume) being typical for most gases. The scanning rate is 20 seconds per point, and the range of analysis is 0–250 ppm (by volume).

The sample line tubing in such illustrative embodiment apparatus is 0.375 inch polypropylene or polytetrafluoroethylene. The sample line inlets are 0.375 inch compression fittings. The electrical supply is 110/220 VAC, 1-phase, 20 amperes. Purge gas in such FT-IR system is nitrogen or clean dry air, at a pressure of 10 psi (0.7 bar). The exhaust pipe of the system is a 1.5 inches NPT pipe. In such embodiment, the FT-IR analysis system may be embodied in a unitary cabinet having a height of 60 inches (1.524 meters), a width of 48 inches (1.219 meters), and a depth of 17 inches (0.432 meter), whereby the footprint of the analyzer unit is sufficiently small to be readily deployed in a semiconductor manufacturing facility or other industrial plant, without undue burden on existing process equipment and facility layout and design.

The illustrative FT-IR analyzer embodiment may utilize any suitable sampling means, as for example an air-driven venturi pump as a motive fluid driver for effecting flow of the sampled gas to the FT-IR cell along a gas flow sample path associated with such cell. Such venturi pump may be arranged with automatic switch-over to a back-up mechanical pump in the event of venturi pump failure or need of supplemental pumping. Alternatively, any other motive fluid driver means may be employed, including for example fans, blowers, impellers, compressors, turbines, cryopumps, peristaltic pumps, ejectors, etc., as may be necessary or desirable in a given end use application of the invention.

Venturi pump operating conditions for the FT-IR system using clean dry air may for example including a pressure of 80 psi (5.5 bar) at a volumetric flow rate of 9 standard cubic feet per minute (SCFM) (255 standard liters per minute (SLM)).

Automatic sample line leak testing may be carried out in the system at regular intervals. In one embodiment of the invention, testing of each sample line tube for leak integrity is carried out on a daily basis.

As a result of the S/N, background drift, and ZPG monitoring by the FT-IR system of the invention, the analysis data for the monitored gas component(s) is of a high accuracy character, there is no signal drift, and the system is always in permanent calibration for all gases.

The system of the invention in one embodiment utilizes a direct measurement FT-IR analyzer of a "double pendulum" type, with a 10 meter gas sample cell. It will be appreciated that the FT-IR system of the invention may be widely varied in construction and arrangement of component parts, while providing the S/N, background drift and ZPG-based detection of the gas components of interest in the monitored environment.

Figure 1:
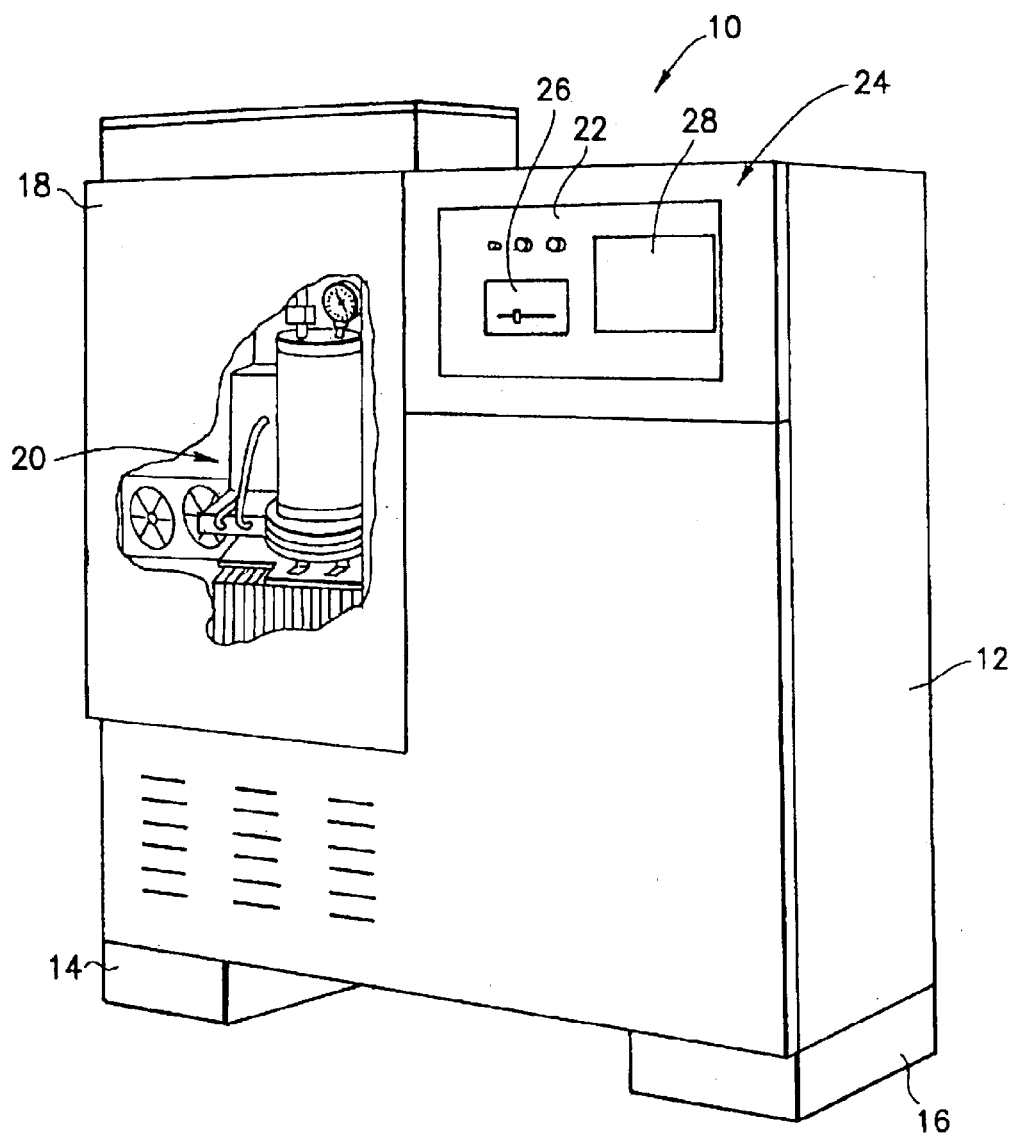
FIG. 1 is a perspective view of an FT-IR toxic gas monitoring apparatus according to one embodiment of the invention.

A schematic representation of an FTIR system 10 according to one embodiment of the invention is shown in FIG. 1, as including a unitary modular housing 12 disposed on feet members 14 and 16 as illustrated. The housing 12 contains the gas sampling and monitoring assembly 20 behind panel 18 of the housing, as shown in the partial breakaway view of the system. The system includes a processor and display unit 24 comprising disk drives 26 and output display screen 28 mounted in face plate 22, and operatively joined in signal transmission relationship with a central processor unit (CPU) in the housing 12, within the interior volume thereof.

The processor and display unit 24 is operatively joined to the gas sampling and monitoring assembly 20, to carry out the analysis and output functions of the system.

Figure 2:
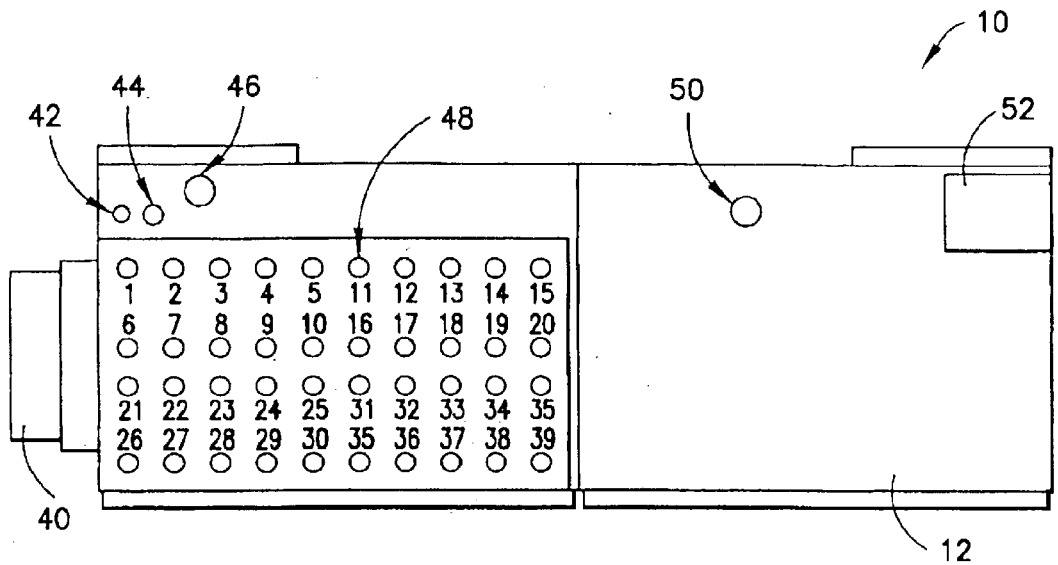
FIG. 2 is a schematic top plan view of the FT-IR toxic gas monitoring apparatus of FIG. 1.

FIG. 2 is a top plan view of the system 10 shown in FIG. 1. The FIG. 2 view shows the top of the housing 12. The system 10 in the view shown has cabinet heat exchanger 40 joined to and extending from the housing 12. The system 10 includes a nitrogen purge port 42, a clean dry air port 44, an exhaust port 46, an AC power coupling 50 and relay/wiring structure 52.

Also shown at the top of the system housing 12 is an array of sample tubes 48, which in the embodiment shown is a 40 sample point array (10 tubes/row×4 tubes/row, in the respective horizontal and vertical rows as illustrated).

Figure 3:
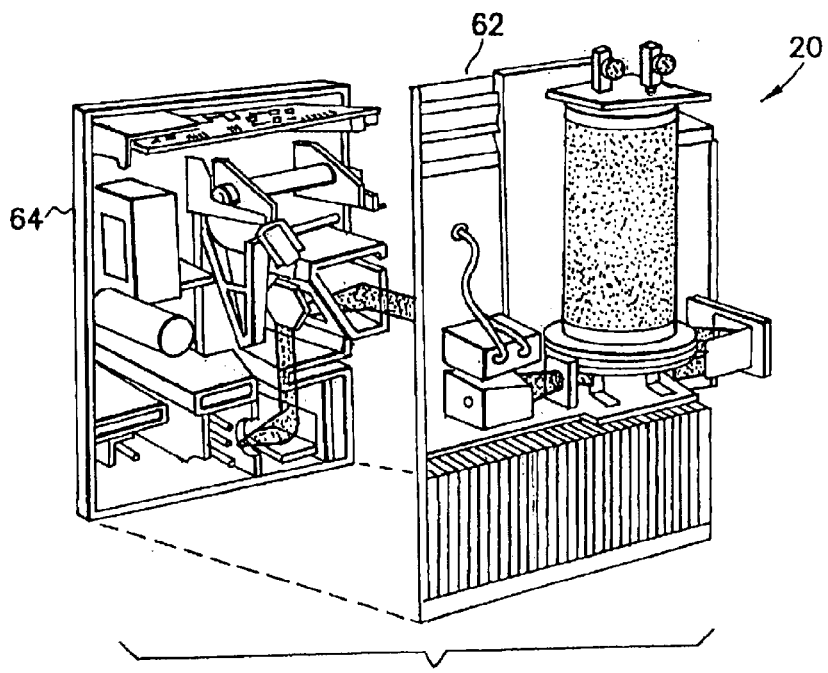
FIG. 3 is a perspective view of internal panels and associated componentry of the FT-IR toxic gas monitoring apparatus of FIG. 1.

FIG. 3 is a perspective view of front and rear panel sub-assemblies 62 and 64, respectively, of the gas sampling and monitoring assembly 20. The front panel subassembly includes the FT-IR cell.

Figure 4:
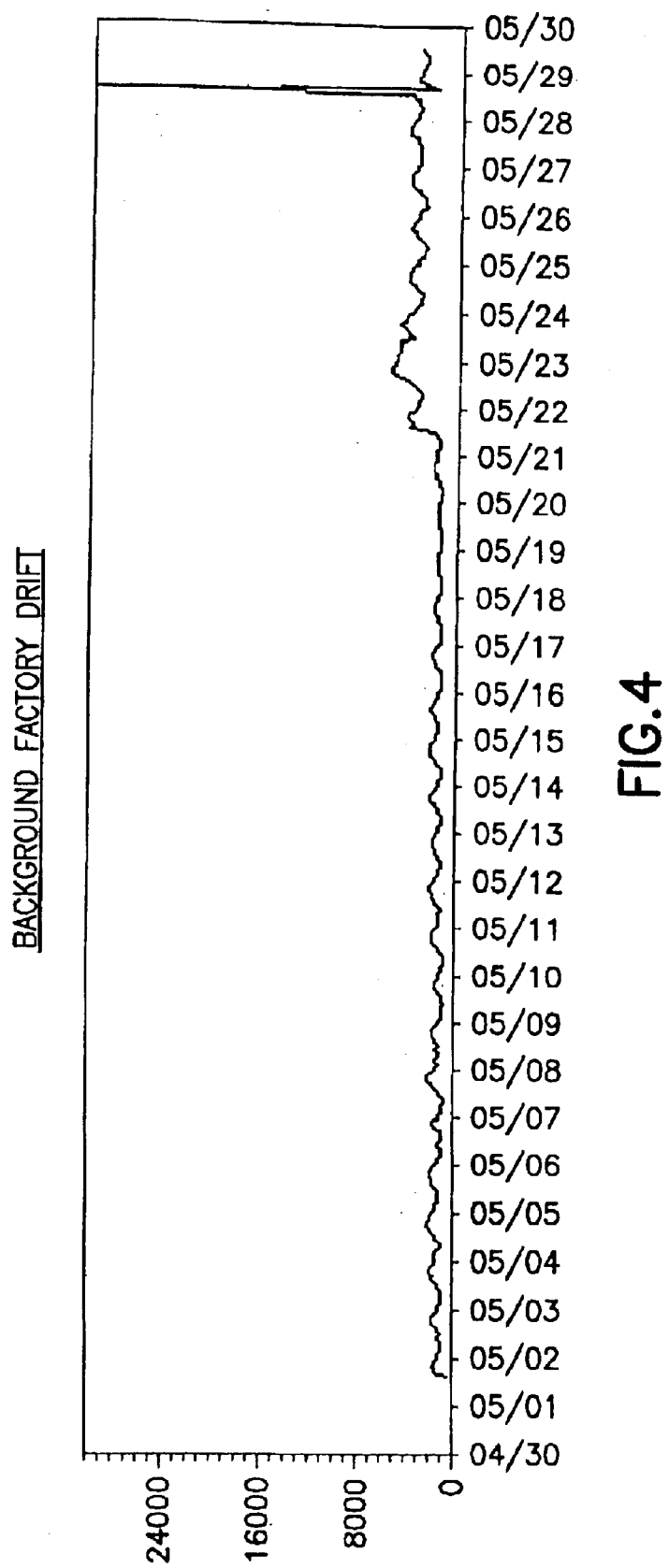
FIG. 4 is a graph of background factory drift as a function of time, for a one-month period of operation of the FT-IR toxic gas monitoring apparatus of the invention, in one embodiment thereof.

FIG. 4 is an illustrative graph of background factory drift as a function of a monthly period for the FT-IR system of the invention, for an illustrative gas component. The background factory drift is shown in FIG. 4 in graphical outputted form, but the specific values are stored in memory of the CPU to provide compensatory adjustment of the output of gas concentration for the specific FT-IR apparatus.

Figure 5:
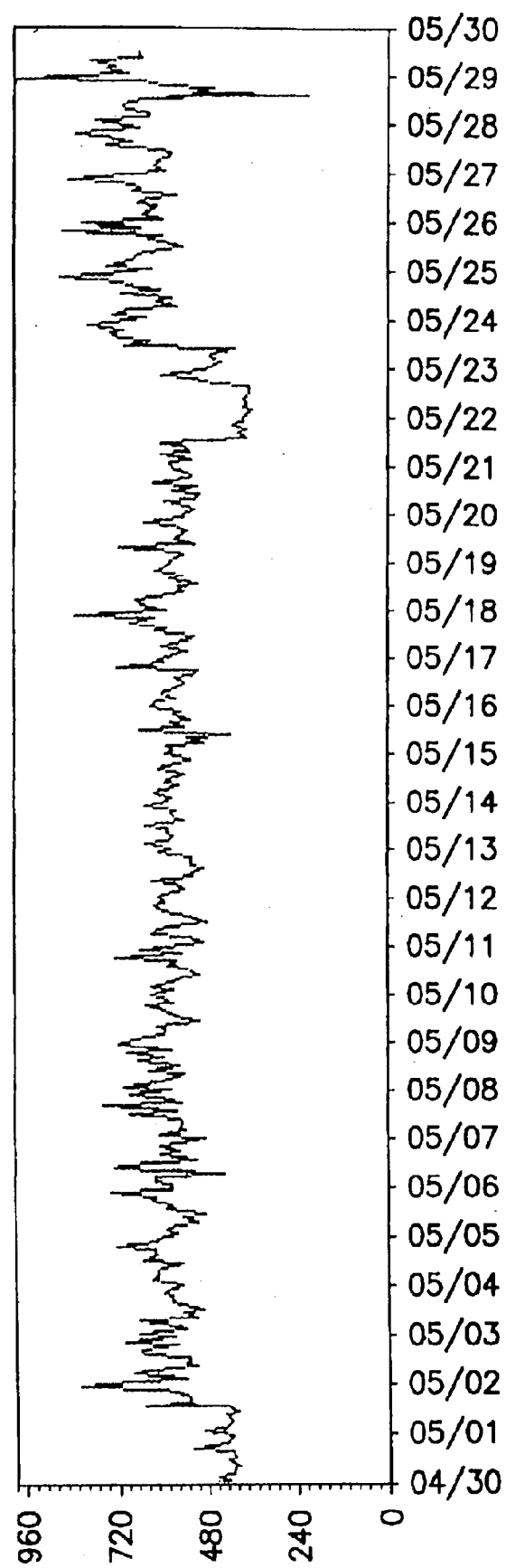
FIG. 5 is a graph of background S/N ratio as a function of time, for a one-month period of operation of the FT-IR toxic gas monitoring system of the invention, in one embodiment thereof.

FIG. 5 is a graph of the background S/N ratio for the FT-IR system of the invention, in an illustrative embodiment thereof, for a particular gas component of interest. As in the case of the background factory drift, the background S/N ratio data is shown in FIG. 4 in graphical outputted form, but the specific values are stored in memory of the CPU to provide appropriate baseline information for determination of gas concentration for the specific FT-IR apparatus.

The concentration of each gas selected for monitoring is calculated from the absorbancies of selected peaks in the sample spectrum and calibration factors using the relatively common P-matrix technique. Calibration factors come from spectra of known gas concentrations. The P-matrix technique, or inverse least squares technique, relates three matricies together:

C=PA
A=absorbance matrix
P=calibration factor matrix
C=concentration matrix

The concentratios of all the gases selected for monitoring can be found by multiplying the matrix of calibration factors by the matrix of absorbances. Or, if the concentrations are and absorbances are known, then calibration factors can be found.

For example, to monitor for 5 gases, 10 spectral windows are used at wavelengths where these gases absorb. At least one window must be selected for each gas but it is more common to select 2 or 3. Then the absorbances in these 10 spectral windows are measured from a spectra taken of the area being monitored. Then these 10 absorbances are multiplied by the 10 calibration factors for each gas and the results for each gas are summed to give gas concentration. Each gas has 10 unique calibration factors.

Along with a spectrometer the toxic gas sensor must have a gas cell to contain the sample gas and to allow the light from the spectrometer to pass through the required path length of sample gas. Longer optical path lengths allow more sample gas molecules to interact with light from the spectrometer resulting in lower detection limits. A 5 to 10 meter path length cell is usuall required to detect gases in the range of 1 ppm. Typical gas cells have mirrors to reflect the light beam back and forth through the cell many times to keep the overall cell dimensions small.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A spectroscopic toxic gas monitoring system for detection of one or more toxic gas species in a fluid environment containing or susceptible to presence of same, said system comprising:
   a spectroscopic monitoring assembly including a gas flow path, a spectroscopic cell in gas flow communication with the gas flow path, an infrared radiation source, an interferometer arranged in receiving relationship to the infrared radiation source to modulate infrared radiation and transmit correspondingly modulated infrared radiation through the spectroscopic cell for absorption of the correspondingly modulated infrared radiation characteristic of said toxic gas species when present in gas flowed through said spectroscopic cell, a detection unit arranged in relation to said spectroscopic cell to receive non-absorbed radiation therefrom and produce a corresponding digitized spectrum for analysis;
   means for sampling the fluid environment and delivering samples therefrom to said gas flow path for flow to the spectroscopic cell; and
   a computational assembly (i) including a stored signal-to-noise ratio reference, and a stored background spectrum for the fluid environment when the toxic gas species is not present therein, and (ii) arranged to analyze the digitized spectrum and responsively produce an output indicative of quantitative presence of the toxic gas species in the fluid environment, in an analysis procedure comprising continuous measurement of the quality of a background spectrum of a monitored spectral region for said fluid environment, and determination of:
   (a) signal-to-noise ratio from signal and noise characteristics of said digitized spectrum, and deviation from the stored signal-to-noise reference;
   (b) a background spectrum for the monitored fluid environment excluding the toxic gas species, if any, therein, and deviation from the stored background spectrum; and
   (c) total detection signal for the detection unit.

2. The spectroscopic toxic gas monitoring system of claim 1, wherein the computational assembly (i) further stores setpoint information for signal-to-noise ratio, and (ii) is constructed and arranged to output a service alert if the deviation of signal-to-noise ratio of said digitized spectrum from the stored signal-to-noise reference deviates from a setpoint determinable from said setpoint information by more than a predetermined extent.

3. The spectroscopic toxic gas monitoring system of claim 1, wherein the computational assembly (i) further stores setpoint information for deviation of background spectrum for the monitored fluid environment excluding the toxic gas species, if any, therein, from the stored background spectrum, and (ii) is constructed and arranged to output a service alert if the deviation of background spectrum for the monitored fluid environment excluding the toxic gas species, if any, therein, from the stored background spectrum, deviates from a setpoint determinable from said setpoint information by more than a predetermined extent.

4. The spectroscopic toxic gas monitoring system of claim 1, wherein the computational assembly (i) further stores setpoint information for the zero path difference, and (ii) is constructed and arranged to output a service alert if the zero path difference deviates from a setpoint determinable from said setpoint information by more than a predetermined extent.

5. The spectroscopic toxic gas monitoring system of claim 1, wherein the computational assembly is constructed and arranged to monitor at least one of (a), (b) and (c) as a function of time, over an extended period of operation, and to provide an output warning a user of gradual degradation of the system and method so that maintenance and/or other compensatory action can be taken.

6. The spectroscopic toxic gas monitoring system of claim 5, wherein the computational assembly is constructed and arranged to monitor each of (a), (b) and (c) as a function of time.

7. The spectroscopic toxic gas monitoring system of claim 1, wherein the computational assembly includes a stored signal-to-noise ratio reference for at least one of toxic gas species selected from the group consisting of ammonia ($NH_3$), arsine ($AsH_3$), boron trifluoride ($BF_3$), boron trichloride ($BCl_3$), carbon monoxide (CO), diborane ($B_2H_6$), dichlorosilane ($SiCl_2H_2$), germane ($GeH_4$), hydrogen bromide (HBr), hydrogen chloride (HCl), hydrogen fluoride (HF), hydrogen selenide ($H_2Se$), methane ($CH_4$), nitric acid ($HNO_3$), nitric oxide (NO), nitrous oxide ($N_2O$), nitrogen dioxide ($NO_2$), nitrogen trifluoride ($NF_3$), phosphine ($PH_3$), phosphorous oxychloride ($POCl_3$), silane ($SiH_4$), silicon tetrafluoride ($SiF_4$), silicon tetrachloride ($SiCl_4$), sulfur hexafluoride ($SF_6$), trichlorosilane ($SiCl_3H$), tungsten hexafluoride ($WF_6$), chloroform ($CHCl_3$), diethyl telluride ($Te(C_2H_5)_2$), hexafluoroethane ($C_2F_6$), hexamethyldisilizane (HMDS), methylsilane ($SiH_3(CH_3)$), dimethylsilane ($SiH_2(CH_3)_2$), trimethylsilane ($SiH(CH_3)_3$), tetramethylsilane ($Si(CH_3)_4$), methyl chloride ($CH_3Cl$), methyl fluoride ($CH_3F$), octoafluorocyclopentene ($C_5F_8$), tert-butyl arsine ($As(t-Bu)H_3$), tert-butyl phosphine ($P(t-Bu)H_3$), tetraethylorthosilicate (TEOS), tetrafluoromethane ($CF_4$), trimethylarsenic ($As(CH_3)_3$), trimethyl borate ($B(CH_3)_3$) and trimethyl phosphite ($P(CH_3)_3$), acetic acid ($CH_3COOH$), ethanolamine, methylene chloride, butyl cellosolve, ethylene glycol monobutyl ether acetate, propylene glycol monomethyl ether acetate, acetonitrile, ethylene glycol monoethyl ether, methyl ethyl ketone, acetone, ethyl acetate, methyl isobutyl ketone, n-butyl acetate, ethanol, n-methyl-2-pyrrolidone, carbon tetrachloride, ethyl beuzene, perchloroethylene, carbon tetrafluoride, ethylene diamine, phenol, cellosolve acetate, ethylene glycol, trichlorobenzene, chlorobenzene, ethyl lactate, 1,1,1-trichloroethane, cyclohexane, formaldehyde, trichloroethylene, cyclohexanone, isopropanol, trifluoromethane, dichlorobenzene, methanol, triethylene glycol, 1,2-dichloroethylene, methyl cellosolve, xylenes (ortho, meta, para), dimethyl acetamide and methyl cellosolve acetate.

8. The spectroscopic toxic gas monitoring system of claim 1, wherein the computational assembly includes a stored signal-to-noise ratio reference for at least one of toxic gas species selected from the group consisting of organic compounds, metalorganic compounds, halocarbon compounds, inorganic halides, inorganic oxides, and inorganic hydrides.

9. The spectroscopic toxic gas monitoring system of claim 1, wherein the computational assembly includes a stored signal-to-noise ratio reference for at least one of toxic gas species selected from the group consisting of toxic gases having a time-weighted average threshold limit value (TWA-TLV) of one part-per-million (ppm) by volume and higher.

10. The spectroscopic toxic gas monitoring system of claim 1, wherein said means for sampling the fluid environment and delivering samples therefrom to said gas flow path for flow to the spectroscopic cell, comprise means for sampling multiple gas species from the fluid environment.

11. The spectroscopic toxic gas monitoring system of claim 1, wherein the computational assembly comprises a computational central processing unit (CPU) that is reprogrammable to add or delete predetermined permanent calibration data for toxic gas species, for adaptation of the system to change in a monitored fluid environment.

12. The spectroscopic toxic gas monitoring system of claim 1, wherein the system does not comprise a pyrolyzer to convert gases to HF for detection.

13. The spectroscopic toxic gas monitoring system of claim 1, wherein said computational assembly comprises dry contact relay outputs including multiple relays, programmable by sample points and gas type(s).

14. The spectroscopic toxic gas monitoring system of claim 1, wherein said computational assembly comprises at least one serial interface port for connection with remote computer and/or printer equipment.

15. The spectroscopic toxic gas monitoring system of claim 1, wherein said at least one serial interface port of said computational assembly comprises an RS-232 port and/or an RS-485 port.

16. The spectroscopic toxic gas monitoring system of claim 1, wherein said at least one serial interface port is coupled with a computational network.

17. The spectroscopic toxic gas monitoring system of claim 1, wherein said computational assembly is adapted to conduct continuous scan spectroscopic analysis.

18. The spectroscopic toxic gas monitoring system of claim 1, wherein the toxic gas species includes a gas species selected from the group consisting of organics, metalorganics, perfluorocarbons (PECs), chlorofluorocarbons (CFCs), hydrofluorocarbons (HFCs), and inorganic gases.

19. The spectroscopic toxic gas monitoring system of claim 1, wherein said output indicative of quantitative presence of the toxic gas species in the fluid environment has a lower detection limit in a range of from about 0.1 to about 2.0 ppm (by volume).

20. The spectroscopic toxic gas monitoring system of claim 1, having a range of analysis of said toxic gas species that is equal to or in a range of from about 0 to about 250 ppm (by volume).

21. The spectroscopic toxic gas monitoring system of claim 1, comprising a unitary cabinet at least partially enclosing each of said spectroscopic monitoring assembly, said means for sampling the fluid environment and delivering samples therefrom to said gas flow path for flow to the spectroscopic cell, and said computational assembly.

22. The spectroscopic toxic gas monitoring system of claim 1, wherein the means for sampling the fluid environment and delivering samples therefrom to said gas flow path for flow to the spectroscopic cell, comprise a motive fluid driver.

23. The spectroscopic toxic gas monitoring system of claim 22, wherein said motive fluid driver comprises a venturi pump.

24. The spectroscopic toxic gas monitoring system of claim 22, wherein said motive fluid driver comprises a mechanical pump.

25. The spectroscopic toxic gas monitoring system of claim 22, wherein said motive fluid driver comprises a venturi pump and a mechanical pump, wherein the venturi pump is operatively coupled with means for automatic switchover to the mechanical pump.

26. The spectroscopic toxic gas monitoring system of claim 22, wherein said motive fluid driver comprises the positive pressure of the gas sample, external to the monitoring system.

27. The spectroscopic toxic gas monitoring system of claim 1, wherein said means for sampling the fluid environment and delivering samples therefrom to said gas flow path for flow to the spectroscopic cell, comprise a sample line at least partially forming said gas flow path, and wherein said system further comprises means for automatic sample line leak testing at predetermined time intervals.

28. The spectroscopic toxic gas monitoring system of claim 1, wherein said output indicative of quantitative presence of the toxic gas species in the fluid environment, is transmitted to control means of a gas-generating or gas-using facility, to responsively control same.

29. The spectroscopic toxic gas monitoring system of claim 28, wherein said control means comprise means selected from the group consisting of alarm and shutdown means, alarm relay and outputting means, flow diversion means, mass flow controllers, and holding tank fill volume controllers.

30. The spectroscopic toxic gas monitoring system of claim 1, coupled in gas monitoring relationship to a semiconductor manufacturing process unit having said fluid environment associated therewith.

31. A semiconductor manufacturing plant including at least one semiconductor manufacturing process unit having a fluid environment associated therewith, and an spectroscopic toxic gas monitoring system as in claim 1, coupled in gas monitoring relationship to said semiconductor manufacturing process unit, to monitor said fluid environment.

32. The semiconductor manufacturing plant of claim 31, wherein the fluid environment comprises a gas stream produced by or used in said semiconductor manufacturing process unit.

33. The semiconductor manufacturing plant of claim 31, wherein the fluid environment comprises an environment selected from the group consisting of gas environments of gas cabinets, process tools, valve manifold boxes, vacuum pumps, and exhaust ducts.

34. A method of toxic gas monitoring for detection of one or more toxic gas species in a fluid environment containing or susceptible to presence of same, said method comprising:
sampling the fluid environment to provide samples for analysis;
spectrometrically analyzing said samples by spectroscopic analysis and generating a corresponding digitized spectrum;
providing a programmable computer including data storage containing a stored signal-to-noise ratio reference, and a stored background spectrum for the fluid environment when the toxic gas species is not present therein;
programmatically analyzing the digitized spectrum via said programmable computer and responsively producing an output indicative of quantitative presence of the toxic gas species in the fluid environment, in an analysis procedure comprising continuously measuring the quality of a background spectrum of a monitored spectral region for said fluid environment, and determining:

(a) signal-to-noise ratio from signal and noise characteristics of said digitized spectrum, and deviation from the stored signal-to-noise reference;

(b) a background spectrum for the monitored fluid environment excluding the toxic gas species, if any, therein, and deviation from the stored background spectrum; and (c) total signal for the spectroscopic analysis.

35. The method of claim 34, wherein the data storage of said programmable computer further stores setpoint information for signal-to-noise ratio, and said computer is programmed to output a service alert if the deviation of signal-to-noise ratio of said digitized spectrum from the stored signal-to-noise reference deviates from a setpoint determinable from said setpoint information by more than a predetermined extent.

36. The method of claim 34, wherein the data storage of said programmable computer further stores setpoint information for deviation of background spectrum for the monitored fluid environment excluding the toxic gas species, if any, therein, from the stored background spectrum, and said computer is programmed to output a service alert if the deviation of background spectrum for the monitored fluid environment excluding the toxic gas species, if any, therein, from the stored background spectrum, deviates from a setpoint determinable from said setpoint information by more than a predetermined extent.

37. The method of claim 34, wherein the data storage of said programmable computer further stores setpoint information for the total signal for the spectroscopic analysis, and said computer is programmed to output a service alert if the total signal deviates from a setpoint determinable from said setpoint information by more than a predetermined extent.

38. The method of claim 34, wherein at least one of (a), (b) and (c) is monitored as a function of time, over an extended period of operation, and an output warning is generated of gradual degradation of output so that maintenance and/or other compensatory action can be taken.

39. The method of claim 34, wherein each of (a), (b) and (c) is monitored as a function of time.

40. The method of claim 34, wherein the data storage of said programmable computer includes a stored signal-to-noise ratio reference for at least one of toxic gas species selected from the group consisting of ammonia ($NH_3$), arsine ($AsH_3$), boron trifluoride ($BF_3$), boron trichloride ($BCl_3$), carbon monoxide (CO), diborane ($B_2H_6$), dichlorosilane ($SiCl_2H_2$), germane ($GeH_4$), hydrogen bromide (HBr), hydrogen chloride (HCl), hydrogen fluoride (HF), hydrogen selenide ($H_2Se$), methane ($CH_4$), nitric acid ($HNO_3$), nitric oxide (NO), nitrous oxide ($N_2O$), nitrogen dioxide ($NO_2$), nitrogen trifluoride ($NF_3$), phosphine ($PH_3$), phosphorous oxychloride ($POCl_3$), silane ($SiH_4$), silicon tetrafluoride ($SiF_4$), silicon tetrachloride ($SiCl_4$), sulfur hexafluoride ($SF_6$), trichlorosilane ($SiCl_3H$), tungsten hexafluoride ($WF_6$), chloroform ($CHCl_3$), diethyl telluride ($Te(C_2H_5)_2$), hexafluoroethane ($C_2F_6$), hexamethyldisilizane (HMDS), methylsilane ($SiH_3(CH_3)$), dimethylsilane ($SiH_2(CH_3)_2$), trimethylsilane ($SiH(CH_3)_3$), tetramethylsilane ($Si(CH_3)_4$), methyl chloride ($CH_3Cl$), methyl fluoride ($CH_3F$), octoafluorocyclopentene ($C_5F_8$), tert-butyl amine ($As(t-Bu)H_3$), tert-butyl phosphine ($P(t-Bu)H_3$), tetraethylorthosilicate (TEOS), tetrafluoromethane ($CF_4$), trimethylarsenic ($As(CH_3)_3$), trimethyl borate ($B(CH_3)_3$) and trimethyl phosphite ($P(CH_3)_3$), acetic acid ($CH_3COOH$), ethanolamine, methylene chloride, butyl cellosolve, ethylene glycol monobutyl ether acetate, propylene glycol monomethyl ether acetate, acetonitrile, ethylene glycol monoethyl ether, methyl ethyl ketone, acetone, ethyl acetate, methyl isobutyl ketone, n-butyl acetate, ethanol, n-methyl-2-pyrrolidone, carbon tetrachloride, ethyl benzene, perchloroethylene, carbon tetrafluoride, ethylene diamine, phenol, cellosolve acetate, ethylene glycol, trichlorobenzene, chlorobenzene, ethyl lactate, 1,1,1-trichloroethane, cyclohexane, formaldehyde, trichloroethylene, cyclohexanone, isopropanol, trifluoromethane, dichlorobenzene, methanol, triethylene glycol, 1,2-dichloroethylene, methyl cellosolve, xylenes (ortho, meta, para), dimethyl acetamide and methyl cellosolve acetate.

41. The method of claim 34, wherein the data storage of said programmable computer includes a stared signal-to-noise ratio reference for at least one of toxic gas species selected from the group consisting of organic compounds, metalorganic compounds, halocarbon compounds, inorganic halides, inorganic oxides, and inorganic hydrides.

42. The method of claim 34, wherein the data storage of said programmable computer includes a stored signal-to-noise ratio reference for at least one of toxic gas species selected from the group consisting of toxic gases having a time-weighted average threshold limit value (TWA-TLV) of one part-per-million (ppm) by volume and higher.

43. The method of claim 34, comprising sampling multiple gas species from the fluid environment.

44. The method of claim 34, wherein said computer comprises a computational central processing unit (CPU) that is reprogrammable to add or delete predetermined permanent calibration data for toxic gas species, for adaptation of the system to change in a monitored fluid environment.

45. The method of claim 34, wherein the method does not comprise use of a pyrolyzer to convert gases to HF for detection.

46. The method of claim 34, wherein said computer is programmed to conduct continuous scan spectroscopic analysis.

47. The method of claim 34, wherein the toxic gas species includes a gas species selected from the group consisting of organics, metalorganics, perfluorocarbons (PFCs), chlorofluorocarbons (CFCs), hydrofluorocarbons (HFCs), and inorganic gases.

48. The method of claim 34, wherein quantitative presence of the toxic gas species in the fluid environment is determined to a lower detection limit in a range of from about 0.1 to about 2.0 ppm (by volume).

49. The method of claim 34, wherein said analysis procedure includes a range of analysis of said toxic gas species that is equal to or in a range of from about 0 to about 250 ppm (by volume).

50. The method of claim 34, wherein said output indicative of quantitative presence of the toxic gas species in the fluid environment, is utilized to responsively control a gas-generating or gas-using facility.

51. The method of claim 34, wherein said fluid environment is associated with a semiconductor manufacturing process.

52. The method of claim 34, wherein said fluid environment is associated with at least one semiconductor manufacturing process unit of a semiconductor manufacturing plant.

53. The method of claim 52, wherein the fluid environment comprises a gas stream produced by or used in said semiconductor manufacturing process unit.

54. The method of claim 52, wherein the fluid environment comprises an environment selected from the group consisting of gas environments of gas cabinets, process tools, valve manifold boxes, vacuum pumps, and exhaust ducts.

* * * * *

UNITED STATES PATENT AND TRADEMARK OFFICE
CERTIFICATE OF CORRECTION

PATENT NO. : 6,862,535 B2
DATED : March 1, 2005
INVENTOR(S) : Robin L. Binder

It is certified that error appears in the above-identified patent and that said Letters Patent is hereby corrected as shown below:

Column 12,
Line 36, ".Sub.2)" should be -- sub.2) --.
Line 38, "SUb.3))" should be -- sub.3)) --.
Lines 40 and 45, "SUb.3)" should be -- sub.3) --.
Line 40, "SUb.4)" should be -- sub.4) --.
Line 53, "beuzene" should be -- benzene --.

Column 16,
Line 7, ".Sub.3)" should be -- sub.3) --.
Line 23, "stared" should be -- stored --.

Signed and Sealed this

Sixteenth Day of August, 2005

JON W. DUDAS
*Director of the United States Patent and Trademark Office*